(12) United States Patent
Fox et al.

(10) Patent No.: US 7,829,873 B2
(45) Date of Patent: Nov. 9, 2010

(54) LOWER SHIELD FOR RADIATION PROTECTION SYSTEM

(75) Inventors: Mark A. Fox, Leesburg, IN (US); James Goldstein, Bloomfield Hills, MI (US)

(73) Assignee: ECO Cath-Lab Systems, Inc., Bloomfield Hills, MI (US)

( * ) Notice: Subject to any disclaimer, the term of this patent is extended or adjusted under 35 U.S.C. 154(b) by 329 days.

(21) Appl. No.: 11/830,219

(22) Filed: Jul. 30, 2007

(65) Prior Publication Data

US 2008/0093568 A1 Apr. 24, 2008

Related U.S. Application Data

(60) Provisional application No. 60/834,351, filed on Jul. 28, 2006.

(51) Int. Cl.
*G21F 7/02* (2006.01)
(52) U.S. Cl. .............. 250/515.1; 250/505.1; 250/517.1; 250/518.1; 250/519.1
(58) Field of Classification Search .............. 250/505.1, 250/515.1, 517.1, 518.1, 519.1
See application file for complete search history.

(56) References Cited

U.S. PATENT DOCUMENTS

| 1,907,523 | A | 5/1933 | Egreesi et al. |
|---|---|---|---|
| 3,299,270 | A | 1/1967 | D'Avella |
| 3,308,297 | A | 3/1967 | Mansker |
| 3,904,695 | A | 9/1975 | Hendricks et al. |
| 3,924,374 | A | 12/1975 | Volper |
| 4,062,518 | A | 12/1977 | Stivender et al. |
| 4,074,141 | A | 2/1978 | Bryant |
| 4,400,623 | A | 8/1983 | Jacobson |
| 4,460,833 | A | 7/1984 | Malamund et al. |
| 4,510,939 | A | 4/1985 | Bernman et al. |
| 4,514,640 | A | 4/1985 | Bagnell et al. |
| 4,581,538 | A | 4/1986 | Lenhart |
| 4,638,166 | A * | 1/1987 | Baudro .................... 250/515.1 |
| 4,729,869 | A | 3/1988 | Schukei et al. |
| 4,741,414 | A | 5/1988 | Claassen |
| 4,905,265 | A | 2/1990 | Cox et al. |
| 4,938,233 | A * | 7/1990 | Orrison, Jr. ................ 128/849 |
| 4,965,456 | A * | 10/1990 | Huettenrauch et al. ... 250/515.1 |
| 4,977,585 | A | 12/1990 | Boyd et al. |
| 4,982,744 | A | 1/1991 | Stanec |
| 5,006,718 | A | 4/1991 | Lenhart |

(Continued)

FOREIGN PATENT DOCUMENTS

DE 1128590 5/1962

OTHER PUBLICATIONS

2003 AADCO Medical catalog (cited in IDS as "Innovative, Ergonomic, Protective Solutions, Rayshield by AADCO Medical Inc. brochure").*

(Continued)

*Primary Examiner*—Jack I Berman
*Assistant Examiner*—Michael Maskell
(74) *Attorney, Agent, or Firm*—SNR Denton US LLC; Brian R. McGinley

(57) ABSTRACT

A radiation protection shield for protecting medical personnel from radiation being applied to a patient positioned on a table. The shield includes a frame and a primary screen including a radiation-resistant material connected to said frame.

21 Claims, 8 Drawing Sheets

U.S. PATENT DOCUMENTS

| | | | |
|---|---|---|---|
| 5,012,114 A * | 4/1991 | Sisson, Jr. | 250/519.1 |
| 5,029,941 A | 7/1991 | Twisselmann | |
| 5,090,044 A | 2/1992 | Kobayashi | |
| 5,138,138 A | 8/1992 | Theilacker et al. | |
| 5,220,175 A * | 6/1993 | Cole | 250/515.1 |
| 5,379,332 A | 1/1995 | Jacobson | |
| 5,417,225 A | 5/1995 | Rubenstein et al. | |
| 5,442,729 A | 8/1995 | Kramer et al. | |
| 5,483,562 A | 1/1996 | Komfeldt et al. | |
| 5,490,716 A | 2/1996 | Naughton | |
| 5,506,882 A | 4/1996 | O'Farrell, Jr. et al. | |
| 5,564,438 A | 10/1996 | Merchant | |
| 5,586,163 A | 12/1996 | Goldstein | |
| 5,613,254 A | 3/1997 | Clayman et al. | |
| 5,632,275 A | 5/1997 | Browne et al. | |
| 5,636,259 A | 6/1997 | Khutoryansky et al. | |
| 5,688,208 A | 11/1997 | Plemmons | |
| 5,842,987 A | 12/1998 | Sahadevan | |
| 5,851,182 A | 12/1998 | Sahadevan | |
| 5,965,829 A | 10/1999 | Haynes et al. | |
| 5,980,472 A | 11/1999 | Seyl | |
| 5,981,964 A * | 11/1999 | McAuley et al. | 250/515.1 |
| 5,994,706 A | 11/1999 | Allen et al. | |
| 6,023,799 A | 2/2000 | Wirth et al. | |
| 6,104,779 A | 8/2000 | Shepherd et al. | |
| 6,105,578 A | 8/2000 | Sommers et al. | |
| 6,224,548 B1 | 5/2001 | Gopinathan et al. | |
| 6,248,064 B1 | 6/2001 | Gopinathan et al. | |
| 6,278,125 B1 | 8/2001 | Belek | |
| 6,282,264 B1 | 8/2001 | Smith et al. | |
| 6,325,538 B1 | 12/2001 | Heesch | |
| 6,334,852 B1 | 1/2002 | Seyl | |
| 6,448,571 B1 * | 9/2002 | Goldstein | 250/515.1 |
| 6,463,701 B1 | 10/2002 | Baloga | |
| 6,481,888 B1 | 11/2002 | Morgan | |
| 6,520,940 B1 | 2/2003 | Gomez | |
| 6,595,918 B2 | 7/2003 | Gopinathan et al. | |
| 6,653,648 B2 * | 11/2003 | Goldstein | 250/515.1 |
| 6,703,632 B1 | 3/2004 | Macklis | |
| 6,835,945 B2 | 12/2004 | Mossor et al. | |
| 6,932,772 B2 | 8/2005 | Goldstein | |
| 7,057,194 B2 * | 6/2006 | Goldstein | 250/515.1 |
| 7,091,508 B2 | 8/2006 | Goldstein | |
| 7,112,811 B2 * | 9/2006 | Lemer | 250/515.1 |
| 2001/0027260 A1 * | 10/2001 | Uematsu et al. | 600/1 |
| 2005/0173658 A1 * | 8/2005 | Lemer | 250/515.1 |
| 2006/0284123 A1 * | 12/2006 | Goldstein | 250/515.1 |
| 2007/0252095 A1 * | 11/2007 | Magram | 250/515.1 |
| 2008/0073593 A1 * | 3/2008 | Fox et al. | 250/503.1 |

OTHER PUBLICATIONS

Balter, "An Overview of Radiation Safety Regulatory Recommendations and Requirements," Catheterization and Cardiovascular Interventions, 1999, pp. 469-474, vol. 47.

Clark, "Editorial Comment: How Much is Too Much?," Catheterization and Cardiovascular Interventions, 2000, p. 285, vol. 51.

Innovative, Ergonomic, Protective Solutions, RayShield® by AADCO Medical Inc. brochure.

Innovative, Ergonomic, Protective Solutions, RayShield® by AADCO Medical Inc. brochure.

Livingston, "Obesity and Its Surgical Management," Am. J. Surg., 2002, pp. 103-113, vol. 184.

Nuclear Associates, "Clear-Pb Lead-Plastic Multipurpose Adjustable-Height Mobile Barrier," 2000, 6 pages, New Jersey, U.S.A.

Podnos et al., "Complications After Laparoscopic Gastric Bypass A Review of 3464 Cases," Arch. Surg., 2003, pp. 957-961, vol. 138.

Ross et al., "Prevalence of Spinal Disc Disease Among Interventional Cardiologists," Am. J. Cardiology, 1997, pp. 68-69, vol. 79.

Randall et al., "Neuro-Oncology Update: Radiation Safety and Nursing Care During Interstitial Brachytherapy," J. Neuroscience Nursing, 1987, pp. 315-320, vol. 19.

Sewchand et al., "Radiation Control in the Intensive Care Unit for High Intensity Iridium-192 Brain Implants," Neurosurgery, pp. 584-588, vol. 20, 1987.

Siemens product catalog entitled Compact and Fast with Universal Application ANGIOSTAR Plus, 22 pages.

Siemens product catalog entitled A Complete New Experience Cardangiography with COROSKOP Plus and BICOR Plus, 14 pages.

Stocker, "Management of the Bariatric Surgery Patient," Endocrinol. Metabl. Clin. N. Am., 2003, pp. 437-457, vol. 32.

Talley et al., "Publications Concerning Costs of Various Cardiovascular Procedures and Drugs," Excerpla Medico, Inc., 1997, pp. 70-72.

Worldwide Innovations & Technologies, Inc., "Breakthrough Technology in Radiation Protection," 3 pages, Kansas, U.S.A.

* cited by examiner

LOWER SHIELD FOR RADIATION PROTECTION SYSTEM

CROSS REFERENCE TO RELATED APPLICATION

This application claims priority from U.S. Provisional Patent Application No. 60/834,351 filed Jul. 28, 2006, which is hereby incorporated by reference including appendices.

BACKGROUND

This invention generally relates to radiation protection systems for protecting medical personnel during radiographic procedures, and more particularly, to a mobile lower shield for use with radiation protection systems.

Radiographic equipment (e.g., x-ray equipment) is used when performing a wide variety of medical procedures. For example, radiographic equipment is used by cardiologists when positioning heart catheters in patients. Many procedures such as these require medical personnel to be in direct contact with the patient, thereby preventing the personnel from being in a separate room and potentially exposing the medical personnel to radiation. Cumulative long-term radiation exposure may cause adverse affects to medical personnel. Medical personnel performing radiographic procedures typically spend many hours over their careers performing such procedures.

Medical personnel often wear protective clothing, including a full lead apron, a thyroid collar and leaded glasses, to reduce radiation exposure while performing the procedures. However, wearing heavy lead protective clothing may have long-term adverse effects, including disabling spinal disorders. Radiation shields are also used during radiographic procedures to reduce radiation exposure.

Radiation shields typically are constructed of materials such as lead that significantly reduce the transmission of radiation. For example, some shields include lead plates mounted on stands that may be adjusted to position the plates between the medical personnel and sources of radiation.

Despite the use of protective clothing and shields, medical personnel are still exposed to radiation. Exposure comes from many radiation sources other than the primary source. For example, a significant secondary radiation source is radiation transmitted through the patient to the medical personnel.

The radiation protection system disclosed in U.S. Provisional Patent Application No. 60/781,262 ('262 application), which is hereby incorporated by reference, solves the aforementioned problems by providing an adjustable and comprehensive barrier to radiation. One embodiment of the radiation protection system according to the '262 application is shown in FIG. 1 of the present application wherein the system is designated in its entirety by reference numeral 10. The system 10 comprises an upper shield, generally designated by 12, including flexible panels 14 and a visually transparent window 16, both of which have low radiation transmissivity, mounted on an upper shield frame 18.

The upper shield 12 is suspended from a lift, generally designated by 20, mounted on an overhead track 22 positioned above a patient support such as a table 24, a radiation source 26, and radiographic monitoring equipment 28 (e.g., cameras, monitors, and audio equipment). During the radiographic procedure, lead blankets 30 are positioned over the patient 32. The flexible panels 14 of the shield 12 may include one or more lower panels 34 extending from the upper shield frame 18 toward the floor 36.

It is important for the system 10 to block radiation radiating below the table 24. A likelihood that radiation will radiate below the table 24 increases when the radiation source 26 is adjusted to extend beneath the table. For example, FIG. 2 illustrates a conventional radiation source 26 (e.g., an x-ray tube 38) connected to an adjustable C-arm 40. As will be apparent to those skilled in the art, the x-ray tube 38 occupies space beneath the table 24 extending beyond the upper shield frame 18 by a considerable distance 42 when the radiation source 26 is positioned adjacent the table 24 and the C-arm 40 is adjusted to position the x-ray tube 38 for a cranial view of the patient 32, as shown in FIG. 2. To protect the medical personnel (not shown) from radiation emitted by the radiation source 26 when the x-ray tube 38 extends beneath the table, the system 10 may include a lateral barrier 42 (shown in FIG. 1) extending below and along a lateral edge of the table 24. The lateral barrier 42 may be integral with the lower panels 34 or the drape blanket 30. When the lateral barrier 42 is integral with the lower panels 34, medical personnel must ensure that the drape blanket 30 overlaps the barrier to prevent radiation from radiating between the barrier and the blanket. A device is sought for use as part of or in combination with shielding systems such as the radiation protection system 10 described in the '262 application to completely block radiation radiating beneath the table 24.

BRIEF DESCRIPTION OF THE DRAWINGS

Corresponding reference characters indicate corresponding parts throughout the several views of the drawings.

DETAILED DESCRIPTION OF EMBODIMENTS

Figure 3:
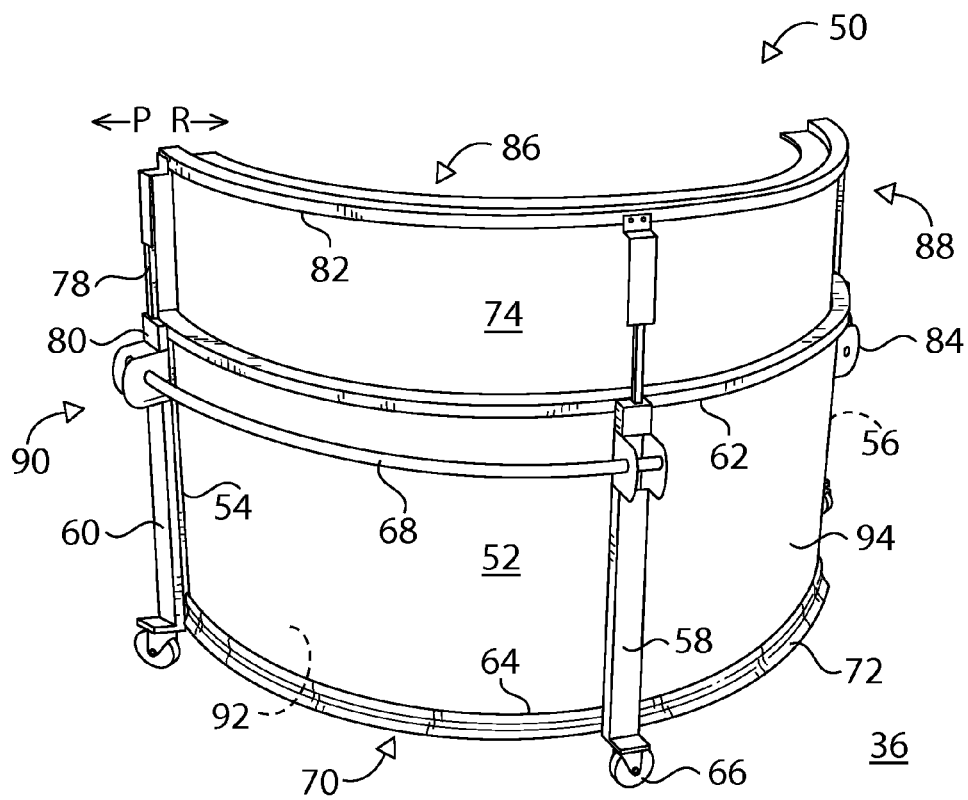
FIG. 3 is a perspective of a lower shield according to a first embodiment of the present invention.
Figure 4:
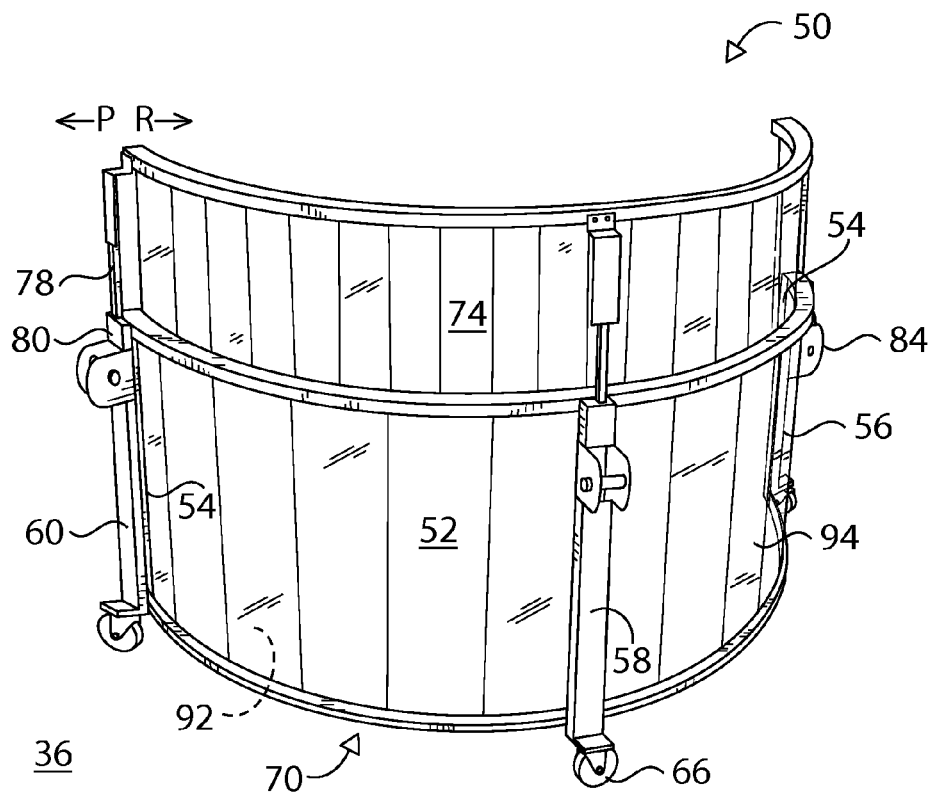
FIG. 4 is a perspective of an alternative first embodiment of the lower shield having a visually transparent screen.

Referring now to the drawings and in particular FIG. 3, a shield according to a first embodiment of the present invention is designated in its entirety by the reference numeral 50. The shield 50 may be part of or used in combination with radiation shielding systems such as the radiation protection system 10 described in the Background section for protecting medical personnel from radiation during a radiological procedure. The radiation protection system 10 and the shield 50 separates the working area (i.e., surgical room) into a radiation side R adjacent the radiation source 26 and a personnel side P opposite the radiation side. The shield 50 includes a lower or primary screen 52. The screen 52 is resistant to x-ray radiation and may be generally impenetrable by radiation. The screen 52 may include a single piece or multiple components. In one embodiment, the screen 52 is made of a unitary thermal-formed piece. In another embodiment, the lower screen 52 includes multiple machined parts connected by a suitable connector such as glue. Variables for determining whether to form the screen 52 from one or multiple pieces include strength, cost of manufacture, and aesthetics. Although the screen 52 may include other materials without departing from the scope of the present invention, in one embodiment the screen includes lead-impregnated acrylic. The screen 52 may be generally visually opaque as shown in FIG. 3, generally visually translucent, or generally visually transparent as shown in FIG. 4.

The primary screen 52 is connected to a lower shield frame 54. The frame 54 may have various configurations without departing from the scope of the invention. The frame 54 includes several components, such as a left vertical support 56, a central vertical support 58, and a right vertical support 60. As shown in FIG. 3, the vertical supports 56, 58, 60 may be connected to each other by an upper support 62 and a lower support 64 extending laterally across the shield 50. In some embodiments, the vertical supports 56, 58, 60 are not connected by lateral frame support elements.

The lower shield frame 54 is mounted on wheels or rollers 66 so the shield 50 can be easily moved over the floor 36 and positioned as desired. Although the shield 50 may include other types of rollers 66 without departing from the scope of the present invention, in one embodiment the rollers comprise casters such as swivel casters. The rollers 66 may include brakes (not shown in detail) for locking the rollers, thereby restricting movement of the shield 50.

As shown in FIG. 3, the lower shield frame 54 may include or be connected to one or more hand rails 68 to facilitate moving the shield 50 to desired positions. For example, during a procedure, medical personnel may desire to move the shield 50 to avoid collisions with the radiation source 26 (not shown in FIG. 3) when the radiation source is moving. In one embodiment (not shown in detail), the shield 50 includes a hand rail 68 on both sides of the screen. The lower shield frame 54 and hand rail 68 may be made of various materials without departing from the scope of the present invention. Variables for determining lower shield frame 54 and rail 68 materials include strength, weight, cost, ease of cleaning, radiation transmissivity, and radiation degradation resistance.

A lower margin 70 (shown in FIG. 4) of the shield 50 may extend down and inward toward the radiation side R of the room (i.e., away from the medical personnel using the shield). Such an angled lower margin 70 allows personnel to stand closer to the shield 50 and patient 32 by receiving toes of the personnel. For embodiments of the shield 50 having a lower frame support 64, as shown in FIG. 3, the frame support may form the lower margin 70.

As shown in FIG. 3, the shield 50 may include a toe drape or flange 72 extending downward from the primary screen 52. The toe drape 72 ensures radiation does not radiate beneath the primary screen 52. The toe drape 72 may be made of various materials without departing from the scope of the present invention. For example, the toe drape 72 may be made of a flexible lead-impregnating material or a rigid radiation-resistant material. The toe drape 72 may be angled toward the radiation side R or the room, away from the medical personnel, thereby allowing the personnel to stand closer to the shield 50 and patient 32 by receiving toes of the personnel. The toe drape 72 may be sized, shaped, and configured in various ways without departing from the scope of the present invention. In one embodiment, the toe drape 72 is sized and shaped to extend down from the primary screen 52 to just above the floor 36 or to slightly contact the floor 36 to ensure radiation does not radiate beneath the toe drape 72. The toe drape 72 may be removable from the primary screen 52 for, for example, cleaning or replacement.

In addition to or instead of a toe drape 72, the shield 50 may include a kick plate (not shown) positioned adjacent the lower edge 70 of the shield 50 to protect the primary screen 52 against wear such as from being damaged from medical personnel, who inadvertently kick the lower shield. Although the kick plate may be made of other materials without departing from the scope of the present invention, in one embodiment the kick plate is made of stainless steel, plastic, or other suitably strong material for protecting the primary screen 52.

Figure 5:
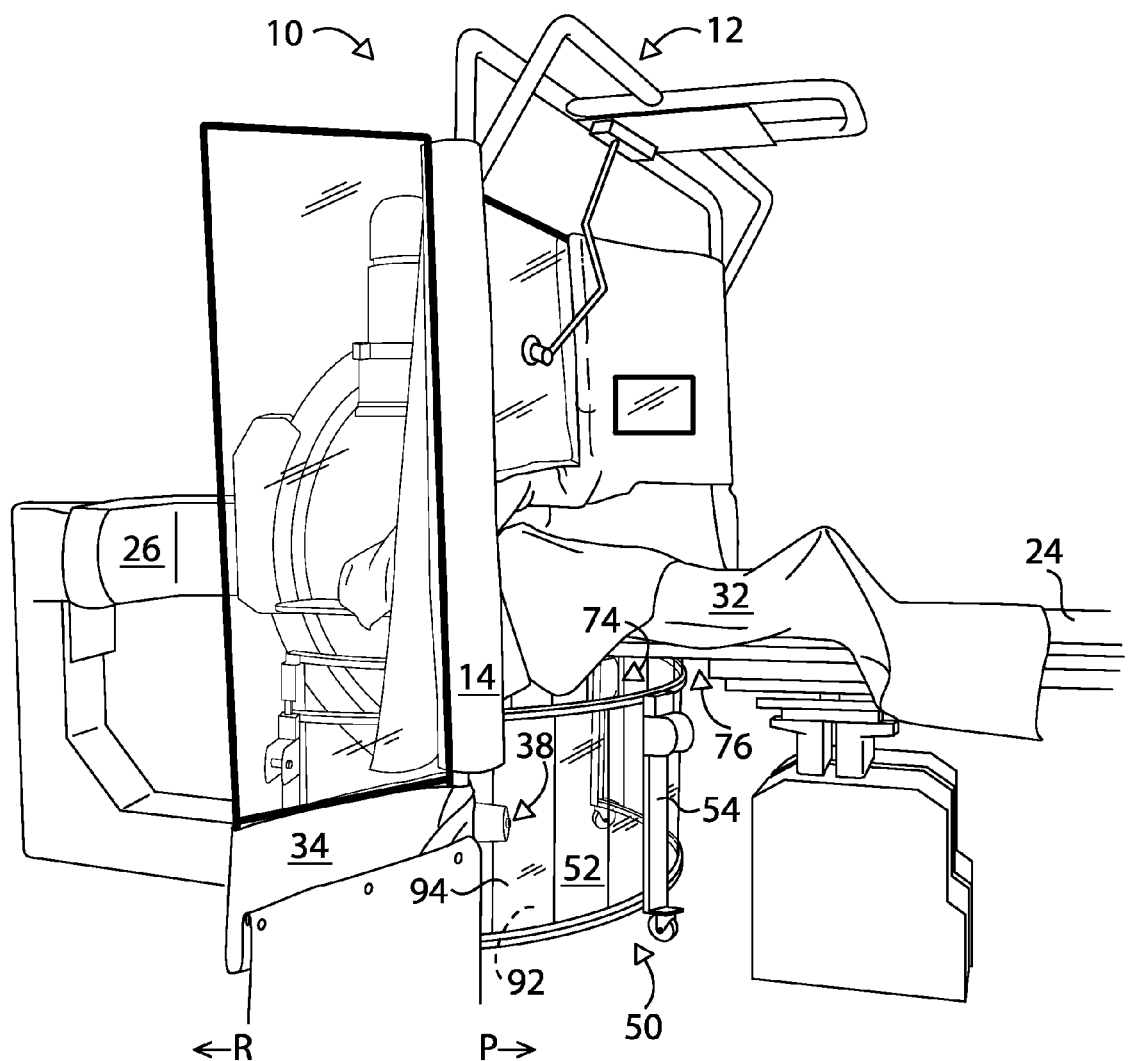
FIG. 5 is a perspective of a radiation protection system of the present invention including a lower shield similar to that shown in FIG. 4 positioned below the table and adjacent the radiation source.

The shield 50 may also include a secondary or upper screen 74 extending above the primary screen 52 to block radiation from radiating above the primary screen when the primary screen does not extend upward to a structure above the screen. For example, when the shield 50 is positioned beneath an adjustable-height table 24, as shown in FIG. 5, the secondary screen 74 may extend above the primary screen 52 to touch a bottom 76 of the table after the table is positioned as desired. The secondary screen 74 extends above the primary screen 52 to contact the table 24 or to a position adjacent the bottom 76 of the table 24. Although the shield 50 may be adjustable to other heights without departing from the scope of the present invention, in one embodiment the shield is adjustable to heights between about 3 feet and about 5 feet.

The secondary screen 74 may be made of the same material as the primary screen 52 or of a different material than the primary screen. For example, in one embodiment both the primary screen 52 and the secondary screen 74 of the shield 50 are made of a lead-impregnated acrylic. The secondary screen 74 may be generally visually transparent, translucent, or opaque.

The primary screen 52 is fixedly connected to the lower shield frame 54, as described above, and the secondary screen 74 is movably connected to the lower shield frame and the primary screen 52. For example, the secondary screen 74 may be slidably connected to the lower shield frame 54. The secondary screen 74 may be movable with respect to the primary screen 52 in a variety of ways without departing from the scope of the present invention. In one embodiment, the secondary screen 74 is fixedly connected to rods 78, which are telescopically received by sleeves 80 fixedly connected to the primary screen 52. The sleeve 80 may be part of or connected to the vertical supports 56, 58, 60 of the frame 54. The rods 78 may be connected by a top support 82 (shown in FIG. 3) extending laterally across the secondary screen 74.

The secondary screen 74 is movable between a fully-extended position, in which the secondary screen is raised by a maximum amount above the primary screen 52 while being slidably connected to the primary screen, and a non-extended position, in which the secondary screen is lowered as far as possible. The secondary screen 74 may also be positioned at various intermediate positions between the fully-extended and non-extended positions with respect to the primary screen 52.

The shield 50 may further include a conventional locking system (not shown in detail) including, for example, detents, brakes, or the like, to secure the secondary screen 74 in position with respect to the primary screen 52. The locking system may include detents or brakes connected to the rods 78 and/or the sleeves 80.

The shield 50 may also include springs 84 connected between the primary screen 52 and contacting the secondary screen 74 to bias the secondary screen upward. The springs 84 may be used in place of or in conjunction with the locking system. In one embodiment, the springs 84 are constant force springs. The springs 84 provide an upward force to bias the secondary screen 74 toward the fully-extended position. When the shield 50 is positioned below the table 24, the springs 84 push the secondary screen 74 upward until the secondary screen contacts the table or reaches the fully extended position. Contacting the bottom 76 of the table 24 with the upward extending secondary screen 74 of the shield 50 ensures radiation does not radiate between itself and the table 24. In one embodiment, the springs 84 provide a neutral balancing force on the secondary screen 74 so it stays in a position when it is moved. In other embodiments, the springs 84 provide a slight upward force or downward force.

The shield 50 may include intermediate components (not shown in detail), other than the springs 84 described above, positioned between the secondary screen 74 and the primary screen 52 to facilitate and/or control movement between the secondary screen 74 and the primary screen 52. Although the shield 50 may include other intermediate components without departing from the scope of the present invention, in one embodiment the shield includes bushings and/or bearings positioned between the screens 52, 74 to facilitate and control relative motion.

The shield 50 may include sealing structures (not shown in detail) between the primary screen 52 and the secondary screen 74. For example, the shield 50 may include gaskets positioned between the screens 52, 74 for blocking radiation from radiating between the screens 52, 74 and may control movement of the upper screen. The sealing structures can control movement of the upper screen 74 by, for example, restricting the upper screen from sliding down.

The locking system described above may be used to keep the secondary screen 74 from rising and/or lowering. For example, although the springs 84 may bias the secondary screen 74 upward whenever an overlying structure such as the table 24 is not impeding movement of the secondary screen and the secondary screen has not reached the fully-extended position, a user may desire to keep the secondary screen from raising beyond a particular point. Locking the secondary screen 74 in a position below the fully extended position may facilitate use of the shield 50 in a variety of ways. For example, locking the secondary screen 74 in position with respect to the primary screen 52 may be helpful for storing the shield 50 by reducing an overall height of the shield. Medical personnel may also lock the secondary screen 74 in place with respect to the primary screen 52 to facilitate positioning of the shield 50 below items such as the patient table 24. Without a locking system to prevent the secondary screen 74 from rising due to spring forces, the user would have to manually hold the secondary screen down against the force of the springs 84 until the shield 50 is positioned beneath the table 24 as desired.

After the shield 50 has been positioned below the table 24 as described, the user can release the locking system or downward manual force on the secondary screen 74 to allow the secondary screen 74 to rise with respect to the primary screen 52. The secondary screen 74 rises until it contacts the bottom 76 of the table 24 or reaches its fully extended position. The upward-biased secondary screen 74 may secure the shield 50 from moving when it is contacting the bottom 76 of the table.

When the secondary screen 74 is pressing against the table 24, and not locked in place, the primary screen 74 rises and lowers as the table is raised or lowered. That is, when the secondary screen 74 is biased upward and contacting the table 24 and the table is raised, the springs 84 continue to push the primary screen upward so that it maintains contact with the table, thereby continuing to block radiation from radiating between the lower shield 52 and the table. When the table 24 is lowered, a downward force of the table on the secondary screen 74 overcomes the upward spring force on the secondary screen so the secondary screen lowers with the table, thereby continuing to block radiation from radiating between the lower shield 52 and the table.

In some embodiments of the present invention, the shield 50 may include or be used in combination with a bumper or roller (not shown) or other shock absorbing or motion-facilitating devices attached to the bottom 76 of the table 24 to ease positioning of the shield 50 beneath the table. For example, the table 24 may be made with such a roller on its under side 76 or be retrofitted onto the bottom of the table. When the shield 50 is positioned beneath the table 24 and the springs 84 are forcing the secondary screen 74 upward against the table, the lower shield may be moved with respect to the table by rolling the secondary screen 74 along the roller beneath the table without having to lower the secondary screen. The roller under the table 24 also protects the bottom 76 of the table from wear and reduces the amount of force required to move the shield 50 during procedures. Reasons for moving the shield 50 during or before a procedure include to position the shield in a desired position and to avoid collision with the radiation source 26. Because parts of the shield 50 such as the springs 84 and under-table roller, the table 24 can be raised and lowered and the lower shield moved along the floor 36 without interruption of blockage of radiation between the shield and the table. The table-bottom roller may be configured in a variety of ways to facilitate use of the shield 50. For example, the table-bottom roller may be configured to allow rolling in one direction, such as a longitudinal direction of the table, or in a plurality of directions including the longitudinal direction and a lateral direction of the table. It is envisioned that the shield 50 may include bumpers, rollers, or other shock absorbing or motion-facilitating devices along a top of the shield in order to facilitate movement of the shield under the table 24.

Figure 1:
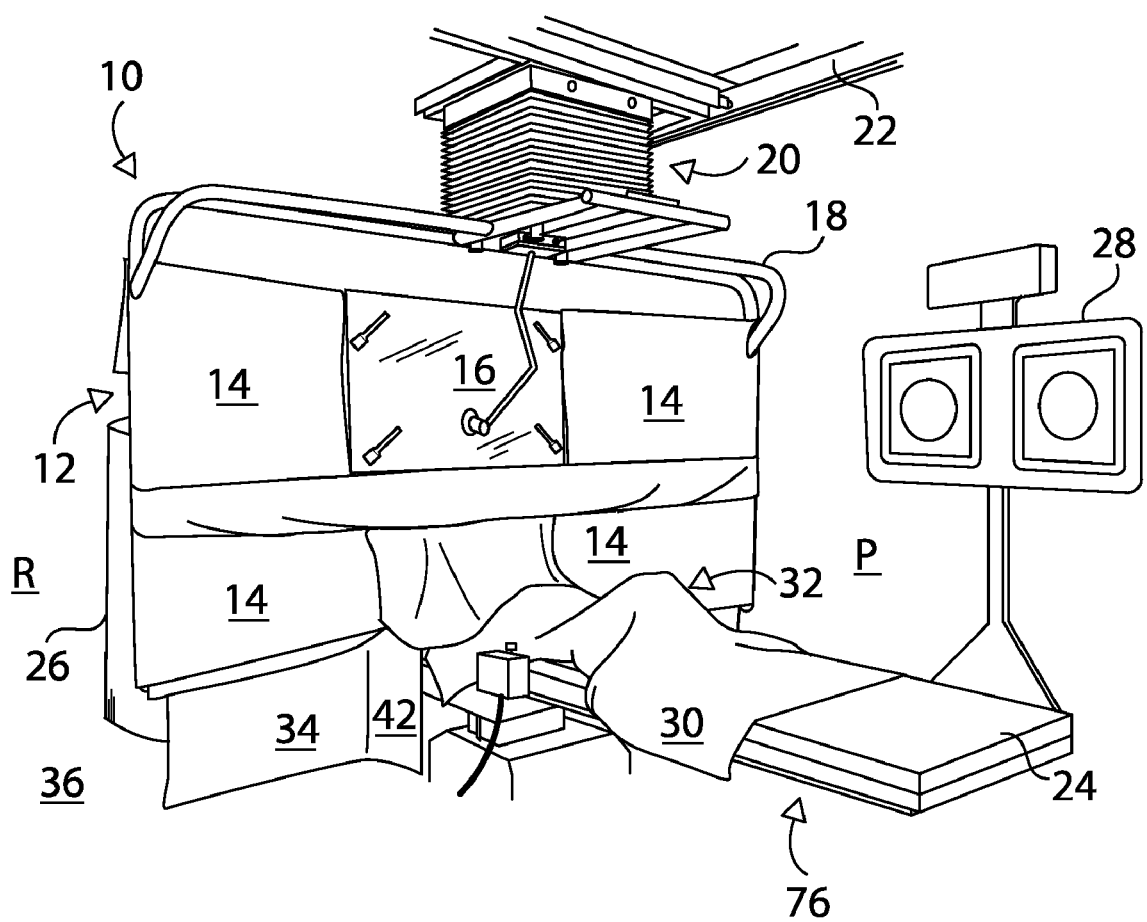
FIG. 1 is a perspective of a radiation protection system positioned above a table holding a patient.

As shown in FIG. 3, the shield 50 may also include an upper flange 86 extending from the top of the shield toward the radiation side R of the procedure room, away from the medical personnel using the shield. The flange 86 reduces secondary radiation scatter to provide added radiation protection for the medical personnel. For example, the flange 86 creates a larger interface between the shield 50 and panels 14 (shown in FIGS. 1 and 5) when the lower shield is positioned below the table 24 and the panels are draped downward adjacent the upper flange 86. The upper flange 86 may extend from side to side along substantially the entire shield 50, as shown in FIG. 3, or extend along a smaller portion of the shield. Although the upper flange 86 may be made of other materials without departing from the scope of the present invention, in one embodiment the upper flange includes a lead impregnated acrylic.

For embodiments of the shield 50 including a secondary screen 74, the upper flange 86 may be an integral part of the secondary screen or attached thereto. For example, the flange 86 may be integral to the top support 82 of the secondary screen 74. For embodiments of the shield 50 including a primary screen 52 but no secondary screen 74, the flange 86 may be an integral part of the primary screen or attached to the primary screen. The flange 86 may be connected to the primary or secondary screen 52, 74 so as to form a generally right angle with whichever screen it is connected to. The upper flange 86 may extend contiguously across the device from a left side 88 of the shield 50 to a right side 90 of the shield or across a portion of the device between the left and right sides.

The shield 50 may have various shapes and sizes without departing from the scope of the present invention. Variables determining the shape and size of the shield 50 include requirements for completely blocking radiation from radiating to the personnel side P of the room when the shield is positioned in the desired position adjacent the radiation source 26. Another variable determining the size and shape of the shield 50 is the sizes and shapes of the spaces it must fit into for use and storage.

The figures illustrate embodiments of the shield in which the lower shield frame 54, the primary screen 52 and the secondary screen 74 are generally curved. For example, the figures illustrate the primary and secondary screen 52 forming a concave inner surface 92 and a convex outer surface 94. In these embodiments, the shield 50 may be positioned adjacent the radiation source 26 so the concave inner surface 92 faces and/or at least partially surrounds the radiation source. The secondary screen 74 may have a shape corresponding to a shape of the primary screen 52 so the secondary screen moves closely adjacent the primary screen when the primary screen is raised and lowered with respect to the primary screen during use of the shield 50.

FIG. 5 illustrates the shield 50 positioned under the table 24 holding the patient 32 and around the radiation source 26. In this position, the shield 50 blocks radiation from radiating out from beneath the table, thereby protecting medical personnel positioned adjacent the patient and table 24 on the personnel side P of the room during the radiographic procedure. The shield 50 may also be positioned adjacent the table 24 without being positioned beneath the table. Whether positioned beneath the table 24, adjacent the table, or both, the shield 50 may be used without the upper shield 12 of the radiation protection system 10. When used in this way, the shield 50 is said to be used as a "stand-alone" radiation protection shield.

The shield 50 can be moved in a variety of ways. For example, medical personnel may pull or push on the hand rail 68 (shown in FIG. 3). Personnel may also push the device with their foot. For example, for embodiments of the shield 50 having a kick plate (not shown) as described above, the personnel may push the kick plate in order to move the lower shield. The shield 50 may also move when contacted by other equipment, whether intentionally or accidentally. For example, the lower shield may be configured and positioned adjacent the patient table 24 so the shield moves along the ground 36 (e.g., on its casters 66) when accidentally contacted by the x-ray tube 38 of the radiation source 26. This mobility protects the shield 50 against damage from unwanted collisions.

In one embodiment of the present invention, the shield 50 is attached to the table 24 and/or to the upper shield 12 of the radiation protection system 10. For example, a top portion of the shield 50 can be connected to the bottom 76 of the table 24, such as by various means. Although the shield 50 may be connected to the table 24 and/or radiation protection system 10 in other ways without departing from the scope of the present invention, in one embodiment the shield is connected to the table and/or radiation protection system by screws, welding or other conventional fasteners. The shield 50 may be connected to the table and/or the upper shield 12 of the radiation protection system 10 during manufacture or thereafter, such as a retrofit.

The shield 50 may be permanently or removably attached to the table 24 and/or the radiation protection system 10. For example, the shield 50 may be attached to the radiation protection system by releasable snaps, clips, hook-and-loop fasteners, or buttons or other conventional releasable fasteners. The shield 50, table 24, and radiation protection system 10, including the fasteners used to connect them, are configured so that radiation is blocked from radiating between the shield and the table and/or system that the shield is attached to.

Although the embodiments of the radiation shield 50 shown and described above include one or two screens 52, 74, shields according to some embodiments of the invention include more than two screens. In one particular embodiment, a lower radiation shield includes three screens: a primary screen (similar to the primary screen 52 described above regarding other embodiments), a secondary screen (similar to the secondary screen 74 described above regarding other embodiments), and a tertiary screen (not shown). The secondary screen is telescopically connected to the primary screen so the secondary screen rises above the primary screen, as described above, and the tertiary screen is telescopically connected to the secondary screen and/or the primary screen so the tertiary screen rises above the secondary screen.

The tertiary screen may be connected to the primary and secondary screens in manners similar to the manners that the secondary screen may be connected to the primary screen, as described above. For example, the tertiary screen may be attached to rods that are slidably received by sleeves connected to the primary and/or secondary screen. Further, the lower shield according to this embodiment may have other similar connection characteristics between the tertiary screen and the other screens including those described above regarding the connection between the secondary and primary screens. For example, the tertiary screen may be spring biased upward and be selectively lockable at various heights. In addition, the tertiary screen may have any of the other characteristics described above regarding the secondary and primary screens. For example, the tertiary screen may be connected to seals, include lead-impregnated acrylic material, be configured for fastening to the table 24 and/or upper shield 12 of the radiation protection system 10, and have bumpers, rollers, and/or shock absorbers for interfacing with the bottom 76 of the table.

The shield according to this embodiment may be positioned beneath the table 24 and beneath the upper shield 12 of the radiation protection system 10, as described above regarding the shield 50 according to the first embodiment. The shield may also be positioned adjacent the table 24 without being positioned beneath the table. Whether positioned below the table 24, adjacent the table, or both, the shield may be used without the upper shield 12 of the radiation protection system 10. When used in this way, the shield is said to be used as a "stand-alone" radiation protection shield.

Although the shield according to this embodiment may adjust to other heights without departing from the scope of the present invention, in one embodiment the shield is adjustable to heights between about 3 feet and about 7 feet. In a particular embodiment, the shield can reach a maximum height above 7 feet, such as between about 7 feet and about a height of a ceiling in the procedure room. Although shields having only two or three screens can reach high heights, such as between about 5 feet and about the ceiling height, a fourth screen may be telescopically connected to one or more of the lower shields (i.e., primary, secondary, and tertiary) for rising above the primary and secondary screens to reach the higher heights.

Figure 2:
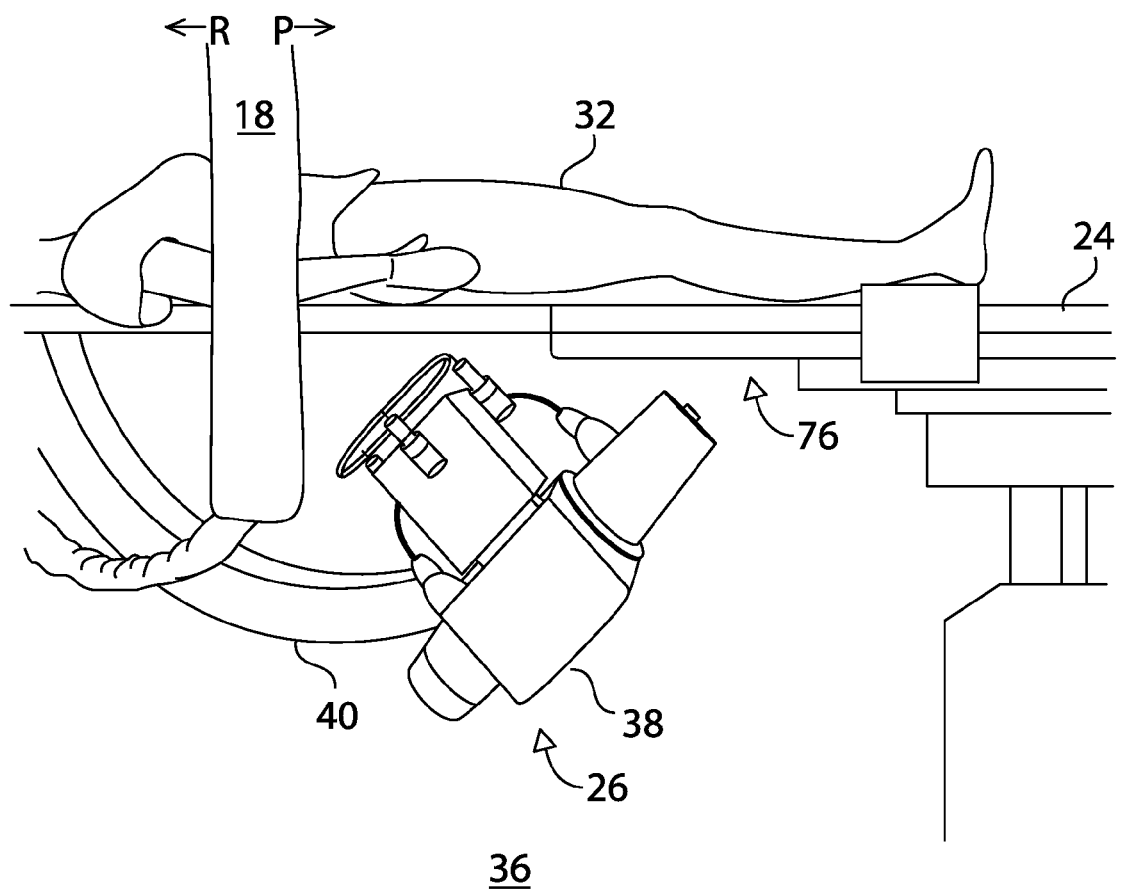
FIG. 2 is a side elevation of a conventional radiation source positioned beneath the table holding the patient.
Figure 6:
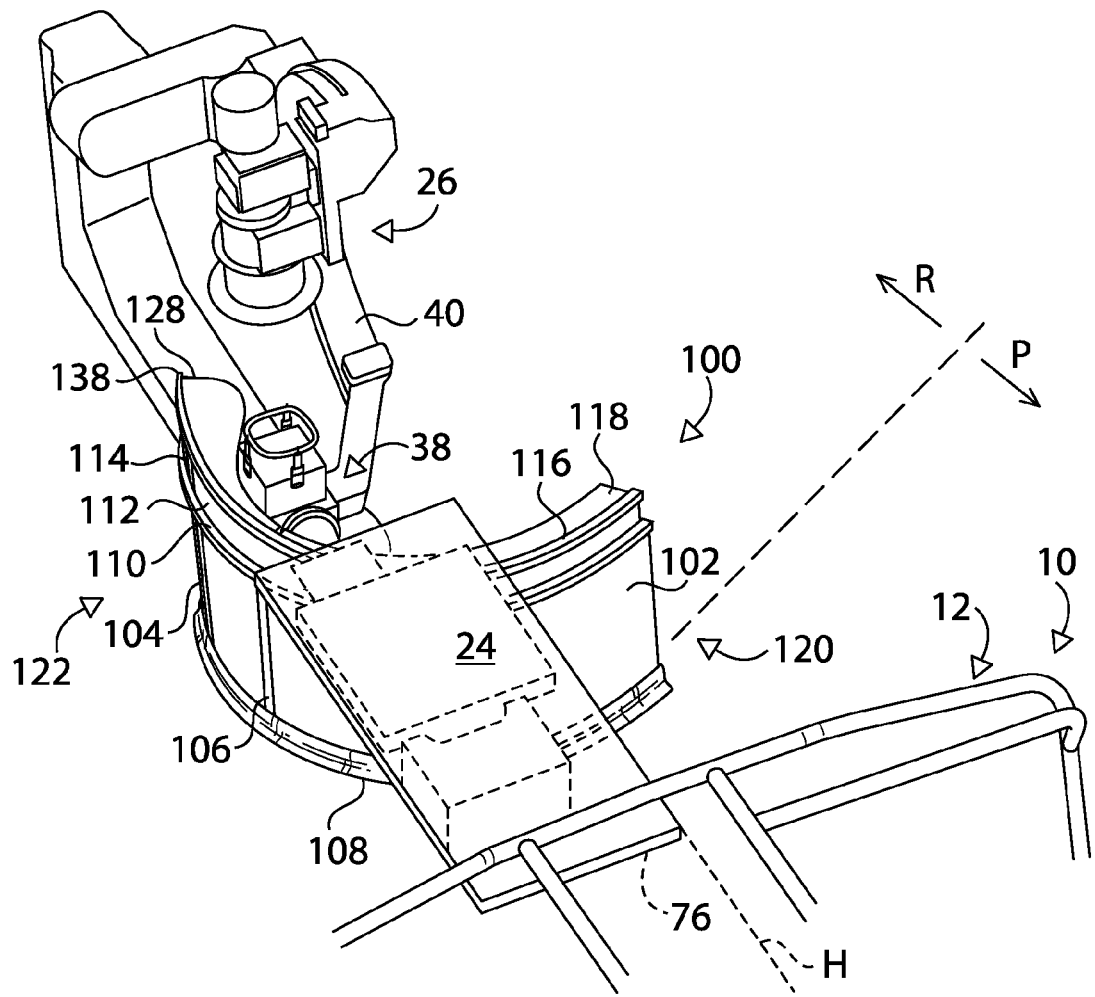
FIG. 6 is a perspective of a lower shield according to a second embodiment of the present invention positioned adjacent the radiation source and below the table.
Figure 7:
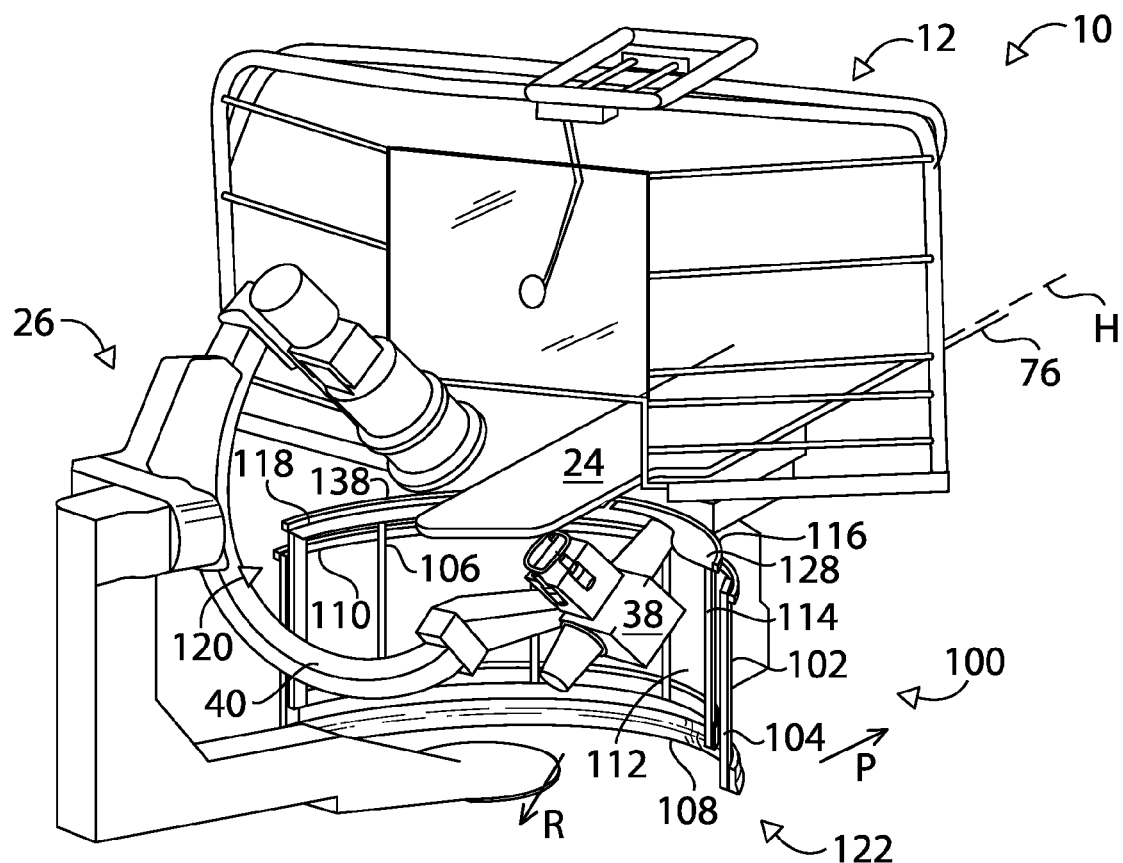
FIG. 7 is another perspective of the lower shield according to the second embodiment positioned adjacent the radiation source and below the table and an upper shield of the radiation protection system.

FIG. 6 illustrates another embodiment of a radiation protection shield 100 according to the present invention. FIG. 6 shows the shield 100 positioned adjacent the radiation source 26 and the table 24. FIG. 7 shows the shield positioned adjacent the radiation source 26, the table 24, and the upper shield 12 of the radiation protection system 10. As described above, the radiation source 26 may include a c-arm 40 supporting an x-ray tube 38. At times during use of the radiation source 26, such as when the radiation source is positioned for a cranial view of the patient, a portion of the x-ray tube 38 is positioned below the table 24. FIGS. 2 and 7 show the x-ray tube 38 positioned below the table 24. The shield 100 is configured to block radiation from radiating from beneath the table 24 in the direction P of medical personnel when positioned adjacent the radiation source 26 and table as desired.

The shield 100 includes a primary screen 102 connected to a frame 104. The frame 104 may include multiple supports such as vertical supports 106, a lower support 108, and an upper support 110. The shield 100 may further include a secondary screen 112 connected to the primary screen. The secondary screen 112 may extend above the primary screen 102 to block radiation from radiating above the primary screen when the primary screen does not extend upward to a structure above the primary screen. For example, when the shield 100 is positioned beneath an adjustable-height table 24, as shown in FIG. 6, the secondary screen 112 may extend above the primary screen 102 to touch a bottom 76 of the table after the table is positioned as desired. The secondary screen 112 extends above the primary screen 102 to contact the table 24 or to a position adjacent the bottom 76 of the table 24.

The secondary screen 112 is connected to a frame 114 including a top support 116 extending laterally across the secondary screen. The secondary screen 112 may be fixed with respect to the primary screen 102 or movable with respect to the primary screen in a variety of ways without departing from the scope of the present invention. The secondary screen 112 may be movable with respect to the primary screen 102 in ways similar to those described above regarding other embodiments of the present invention. For example the secondary screen 112 may be fixedly connected to rods (similar to the rods 78 shown in FIGS. 3 and 4), which are telescopically received by portions of the frame 104 of the primary screen 102.

The shield 100 may include an upper flange 118 extending from a top region of the shield, such as from the top support 116 of the shield, toward the radiation side R of the procedure room, away from the medical personnel using the shield. For embodiments of the shield 100 having a primary screen 102 but no secondary screen 112, the upper flange 118 extends from the primary screen adjacent a top region of the primary screen, such as from the upper support 110 of the frame 104 of the primary screen. For embodiments of the shield 100 having a primary screen 102, a secondary screen 112, and a tertiary screen, as described above, the upper flange 118 extends from the tertiary screen adjacent a top region of the tertiary screen. The flange 118 reduces secondary radiation scatter to provide added radiation protection for the medical personnel as described above regarding the upper flange of other embodiments of the invention.

Figure 8:
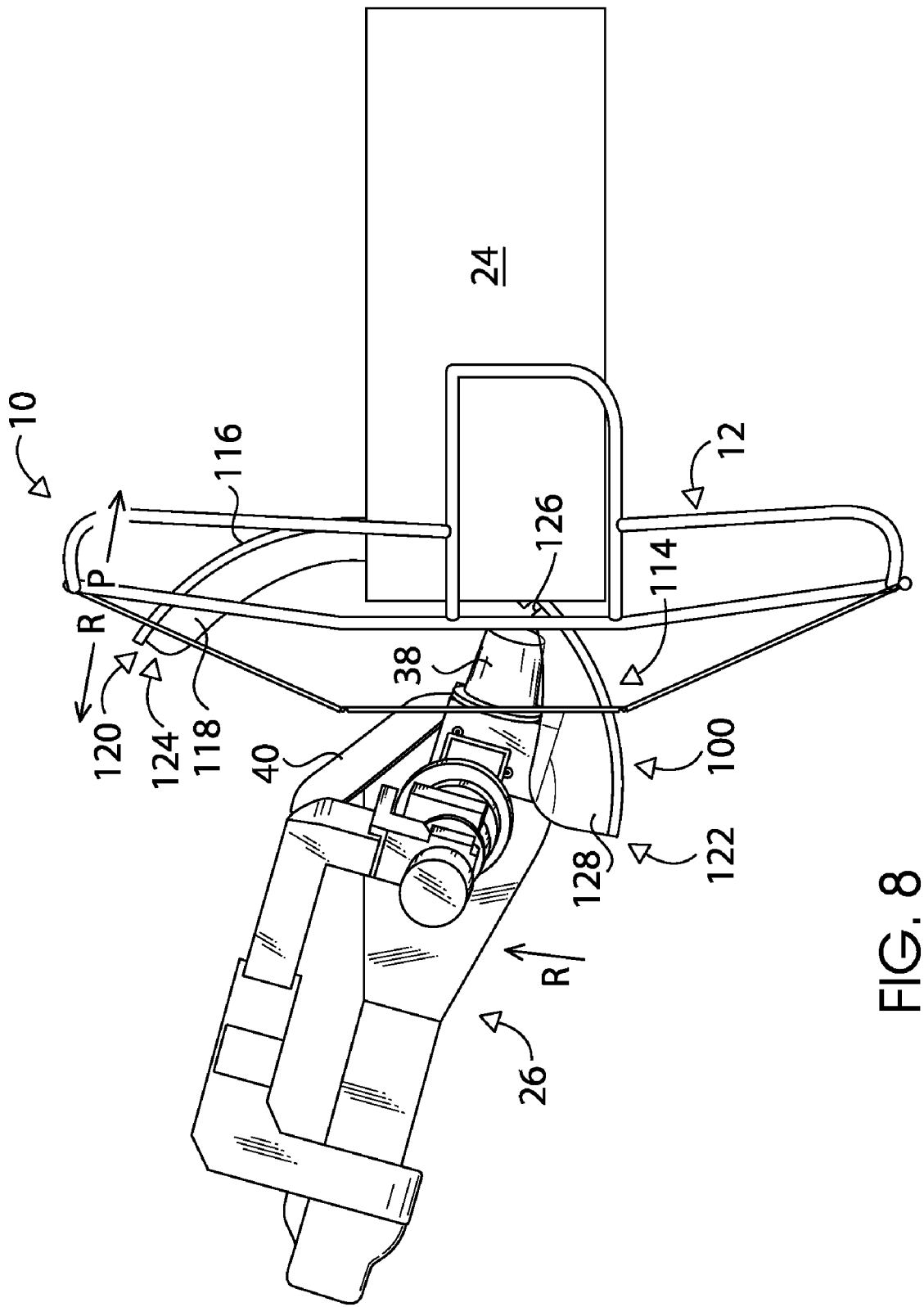
FIG. 8 is a top plan of the lower shield according to the second embodiment positioned adjacent the radiation source and below the table and the upper shield of the radiation protection system.

The upper flange 118 may extend contiguously across the device from a left side 120 of the shield 100 to a right side 122 of the shield or across a portion of the device between the left and right sides. For example, as illustrated in FIG. 8, the upper flange 118 may extend from a left end 124 adjacent the left side 120 of the shield 100 to a right end 126 opposite the left end. The upper flange 118 may be made of various radiation-resistant materials. Although the upper flange 118 may be made of other materials without departing from the scope of the present invention, in one embodiment, the upper flange includes a lead-impregnated acrylic.

The shield 100 according to this embodiment also includes an upper deflector or shelf 128 extending from the top region of the shield, such as the top support 116 of the shield, toward the radiation side R of the procedure room, away from the medical personnel using the shield. For embodiments of the shield 100 having a primary screen 102 but no secondary screen 112, the upper shelf 128 extends from the primary screen adjacent the top region of the primary screen, such as the upper support 110 of the frame 104. For embodiments of the shield 100 having a primary screen 102, a secondary screen 112, and a tertiary screen, as described above, the upper shelf 128 extends from the tertiary screen adjacent a top region of the tertiary screen. The shelf 128 reduces secondary radiation scatter to provide added radiation protection for the medical personnel. It is contemplated that the shelf 128 may be part of the upper flange 118. For example, the upper flange 118 may include a protruding portion (i.e., the shelf) adjacent a side of the shield 100 (e.g., the right side 122). The upper shelf 128 may be made of various radiation-resistant materials. Although the shelf 128 may be made of other materials without departing from the scope of the present invention, in one embodiment, the upper shelf includes a lead-impregnated acrylic.

The shelf 128 may have various shapes and sizes and be located at various locations along the top support 116 without departing from the scope of the present invention. In general, the shelf 128 is sized, shaped, and located along the top support 116 for blocking radiation radiating below the table 24, thereby protecting medical personnel from exposure. FIG. 8 shows the shelf 128 located adjacent the right side 122 of the shield 100 and extending farther from the top support 116 toward the radiation side R than the upper flange 118 extends from the top support toward the radiation side.

Figure 9:
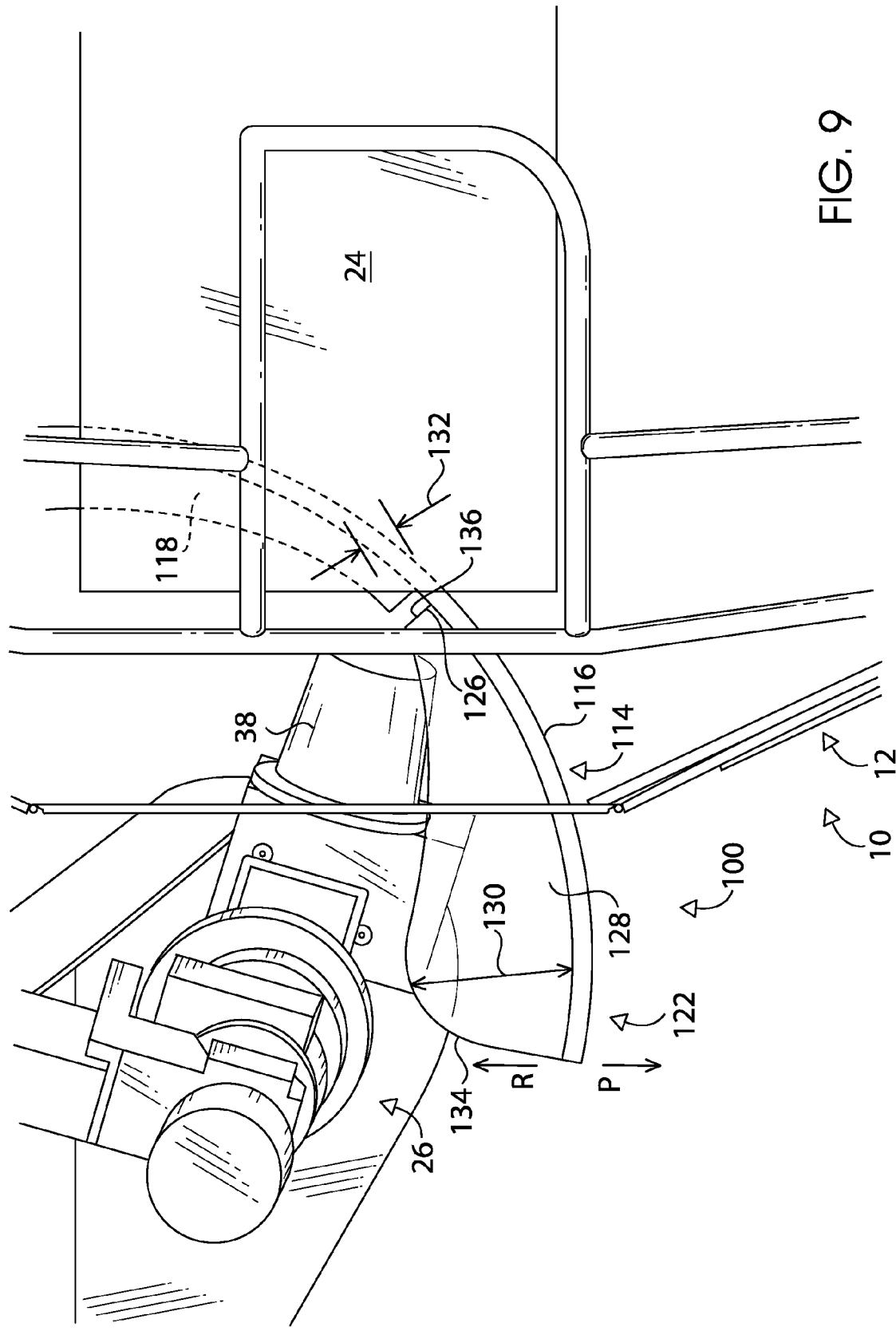
FIG. 9 is an enlarged top plan of the lower shield according to the second embodiment positioned adjacent the radiation source and below the table and the upper shield of the radiation protection system.

When the shield 100 is positioned under the table 24 with the sides 120, 122 extending from beneath the table, the upper shelf 128 provides extra shielding (i.e., in addition to the screens 102, 112) to block radiation from radiating to the personnel side P of the shield. It is contemplated that the shield 100 may include more than one shelf 128, such as one shelf positioned adjacent each side 120, 122 of the shield. As shown in FIGS. 8 and 9, the upper shelf 128 may be positioned adjacent an end (e.g., the right end 126) of the upper flange 118 and, to ensure radiation does not emit between the upper shelf and the upper flange, the shelf may overlap the upper flange.

FIGS. 6-9 illustrate the shield 100 positioned under the table 24 and around the radiation source 26. In this position, the shield 100 blocks radiation from radiating out from beneath the table, thereby protecting medical personnel positioned adjacent the patient and table 24 on the personnel side P of the room during the radiographic procedure. The shield 100 may also be positioned adjacent the table 24 without being positioned beneath the table. Whether positioned beneath the table 24, adjacent the table, or both, the shield 100 may be used without the upper shield 12 of the radiation protection system 10. When used in this way, the shield 100 is said to be used as a "stand-alone" radiation protection shield.

The upper flange 118 and the upper shelf 128 may extend from the secondary screen 112 at various angles with respect to the primary screen 102 and the secondary screen. For example, as shown in FIGS. 6 and 7, the upper flange 118 and the upper shelf 128 may extend from the top support 116 at about a right angle with respect to the primary and secondary screens 102, 112. In other embodiments (not shown), the upper flange 118 and/or the upper shelf 128 extend from the top support 116 to form angles with the primary and secondary screens 102, 112 of greater than or less than 90°.

The shelf 128 may have a varying width, such as varying from a maximum width 130 and a minimum width 132 (shown in FIG. 9). As shown in FIG. 9, the shelf 128 may be wider adjacent an outer end 134 than it is adjacent an inner end 136 opposite the outer end. A primary variable determining the shape and size of the shelf 128 is an ability of the shelf to block radiation emitted below the table 24. Thus, the shelf 128 is sized, shaped, and positioned on the shield 100 so the shelf blocks as much radiation as possible from being emitted to the personnel side P of the room.

As illustrated in FIGS. 6 and 7, the top support 116 may include an elevated portion 138 from which the upper shelf 128 extends. The secondary screen 112 is sized and shaped to fill the additional area formed by the elevated portion 138 of the top support 116. The elevated portion 138 of the top support 116 may be positioned generally at or above a height H of a top surface of the table 24. The elevated portion 138 may be elevated above the top support 116 by various amounts without departing from the scope of the present invention. In one embodiment the elevated portion 138 is raised by a distance that is at least equal to a thickness of a bed of the table so that when the top support contacts the bottom 76 of the table 24, the elevated portion may be positioned adjacent the table and at the least reach the height H of the top of the table.

The elevated position of the shelf 128 has functional benefits including increased facility of positioning the shield 100 adjacent the table 24. Specifically, when positioning the shield 100 adjacent the table 24, medical personnel may position the elevated portion 138 of the top support 116 and/or the shelf 128 beside the table to fill a gap that might otherwise be present between the shield 100 and the table and/or the shield and the upper shield 12. For example, personnel may know that the shield 100 is positioned as desired when the upper portion 138 of the top support 116 touches an edge of the table 24.

An elevated shelf 128 may block more radiation than a shelf located on the shield 100 so that it is positioned below the table during use. For example, if the shelf 128 was positioned below the table, much of the radiation that it would block would have been blocked by the table 24 anyway. Further, personnel may use the shelf 128 for holding items such as notes or surgical implements. The shield 100 according to this embodiment is otherwise identical to previously described embodiments and, therefore, will not be described in further detail.

As will be appreciated by those skilled in the art, the systems described above may be included in new radiographic labs or retrofitted to existing labs.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

The invention claimed is:

1. A radiation protection shield for protecting medical personnel from radiation being applied to a patient positioned on a table, the shield comprising:
    a frame having a plurality of vertical supports that divide a radiation-source side of the frame from a user side of the frame;
    a primary screen including a radiation-resistant material, the primary screen connected to said frame;
    a secondary screen slidably connected to the primary screen so that the secondary screen is moveable along a plane defined by the plurality of vertical supports to one of a retracted configuration and an extended configuration; and
    an upper flange extending (i) across at least a portion of the frame and (ii) from a top region of the secondary screen and towards the radiation-source side of the frame, the upper flange effective in reduction of radiation scatter;
    wherein the upper flange effectuates reduction of radiation scatter in both of the first retracted configuration and the extended configuration; the shield further comprising a shelf having (i) a shelf outer end on a side of the shelf adjacent to an outer end of the frame and (ii) a shelf inner end on a side of the shelf opposite to the shelf outer end, the shelf having a varying width that is wider at the shelf outer end than the shelf inner end.

2. The radiation protection shield as set forth in claim 1, wherein the primary screen includes a lead-impregnated acrylic.

3. The radiation protection shield as set forth in claim 1 further comprising:
    a plurality of rollers attached to a bottom of the frame to allow a lower shield to move along a floor that the shield is positioned on during use of the radiation protection shield.

4. The radiation protection shield as set forth in claim 3, wherein said rollers are lockable to restrict the rollers from moving thereby limiting movement of the lower shield.

5. The radiation protection shield as set forth in claim 1, wherein the secondary screen includes a lead-impregnated acrylic.

6. The radiation protection shield as set forth in claim 1, wherein:
    the primary screen and secondary screen are curved forming an inner concave surface on the radiation-source side of the frame and an outer convex surface opposite the concave surface on the user side of the frame; and
    the inner surface is positioned adjacent a radiation source during use of the system.

7. The radiation protection shield as set forth in claim 1 further comprising:
    a hand rail connected to said primary screen to facilitate moving of a lower shield.

8. The radiation protection shield as set forth in claim 1 further comprising:
    a toe flange extending downward from the primary screen.

9. The radiation protection shield as set forth in claim 1 further comprising:
    a kick plate positioned adjacent a lower edge of the shield for protecting the primary screen and for medical personnel to use to move a lower shield.

10. The radiation protection shield as set forth in claim 1 further comprising:
    an upper flange extending from a top region of the shield to form a right angle with the primary screen.

11. The radiation protection shield as set forth in claim 1, further comprising:

an upper flange extending from a top region of the shield to form a right angle with the secondary screen.

12. The radiation protection shield as set forth in claim 11 further comprising:
an upper shelf extending from the top region of the shield adjacent said upper flange to form a right angle with the secondary screen.

13. The radiation protection shield as set forth in claim 12, wherein said upper shelf extends farther from the secondary screen than the upper flange extends from the secondary screen.

14. The radiation protection shield as set forth in claim 12, wherein the upper shelf is positioned adjacent an end of said shield.

15. The radiation protection shield as set forth in claim 14 further comprising:
an upper shelf extending from a top region of the shield.

16. The radiation protection shield as set forth in claim 15, wherein said shelf includes a lead-impregnated acrylic.

17. The radiation protection shield as set forth in claim 1, wherein,
the secondary screen is connected to the plurality of vertical supports; and
the frame includes sleeves receiving the plurality of vertical supports.

18. The radiation protection shield as set forth in claim 17 further comprising:
springs attached to the frame adjacent said sleeves for providing an upward force to the secondary screen by way of said rods.

19. The radiation protection shield as set forth in claim 17 further comprising:
a locking mechanism attached to the frame adjacent said sleeves for selectively locking the rods in place in the sleeves thereby locking the secondary screen in place with respect to the primary screen.

20. A radiation protection shield for protecting medical personnel from radiation being applied to a patient positioned on a table, the shield comprising:
a frame having a radiation-source side and a user side;
multiple screens telescopically connected to each other in a vertical direction along the frame so that an overall height of the shield can be selectively adjusted during use of the shield,
an upper flange extending (i) across a first portion of the frame and (ii) from a top region of the secondary screen and towards the radiation-source side of the frame, the upper flange effective in reduction of radiation scatter, and
a shelf extending (i) across a second portion of the frame and (ii) from the top region of the secondary screen and towards the radiation-source side of the frame, the shelf having (i) a shelf outer end on a side of the shelf adjacent to an outer end of the frame and (ii) a shelf inner end on a side of the shelf opposite to the shelf outer end, the shelf having a varying width that is wider at the shelf outer end than the shelf inner end.

21. A radiation protection shield as set forth in claim 1, further comprising:
a toe drape angled toward the radiation-source side of the frame.

* * * * *